United States Patent
Augustine et al.

(10) Patent No.: US 6,464,666 B1
(45) Date of Patent: Oct. 15, 2002

(54) INTRAVENOUS FLUID WARMING CASSETTE WITH STIFFENING MEMBER AND INTEGRAL HANDLE

(75) Inventors: Scott D. Augustine, Bloomington; Scott A. Entenman, St. Paul; Keith J. Leland, Plymouth; Gary R. Maharaj, Eden Prairie; Teryl L. Woodwick-Sides, Maple Grove, all of MN (US)

(73) Assignee: Augustine Medical, Inc., Eden Prairie, MN (US)

( * ) Notice: Subject to any disclaimer, the term of this patent is extended or adjusted under 35 U.S.C. 154(b) by 0 days.

(21) Appl. No.: 09/415,405

(22) Filed: Oct. 8, 1999

(51) Int. Cl.⁷ .................................................. A61F 7/12
(52) U.S. Cl. ...................................... 604/113; 392/470
(58) Field of Search .............................. 604/93.01, 113, 604/114, 6.13, 122–127, 403, 408; 392/465, 470; 165/46; 222/146.1, 146.2, 146.5

(56) References Cited

U.S. PATENT DOCUMENTS

| | | | |
|---|---|---|---|
| 3,140,716 A | | 7/1964 | Harrison et al. |
| 3,485,245 A | | 12/1969 | Lahr et al. |
| 4,131,200 A | | 12/1978 | Rinfret |
| 4,602,910 A | | 7/1986 | Larkin |
| 4,707,587 A | * | 11/1987 | Greenblatt |
| 4,731,072 A | * | 3/1988 | Aid ............................ 604/408 |
| 4,919,134 A | | 4/1990 | Streeter |
| 4,919,326 A | | 4/1990 | Deiger |
| 5,098,202 A | | 3/1992 | Rosenbaum |
| 5,102,234 A | | 4/1992 | Levy |
| 5,245,693 A | | 9/1993 | Ford et al. |
| 5,381,510 A | * | 1/1995 | Ford et al. ................... 165/169 |
| 5,423,421 A | | 6/1995 | Inoue et al. |
| 5,520,975 A | | 5/1996 | Inoue et al. |
| 5,733,619 A | | 3/1998 | Patel et al. |
| 5,792,526 A | | 8/1998 | Watanabe et al. |
| 5,865,309 A | | 2/1999 | Futagawa et al. |
| 5,875,282 A | * | 2/1999 | Jordan et al. ................ 165/170 |

FOREIGN PATENT DOCUMENTS

| | | |
|---|---|---|
| EP | 01 96 191 A1 | 5/1982 |
| EP | 0 119 469 | 2/1983 |
| EP | 0 095 526 A2 | 12/1983 |

OTHER PUBLICATIONS

Brochure for "The Medi–Temp™II GAYMAR®Blood/Fluid Warmer", Gaymar Industries, Inc.

* cited by examiner

*Primary Examiner*—Brian L. Casler
*Assistant Examiner*—Catherine Serke
(74) *Attorney, Agent, or Firm*—Gray Cary Ware & Freidenrich

(57) ABSTRACT

A fluid warming cassette with a stiffening frame structure and an integral handle is provided to support a parenteral fluid container. The fluid container is desirably thin to minimize heat exchange inefficiencies. The frame structure permits the thin fluid container to be inserted into the narrow space between fixed position warming plates of a warming unit. The frame structure has a quadrilateral shape with sides and ends. The fluid container is attached, at its periphery to the sides and ends of the frame structure, within the quadrilateral shape. Part of the frame structure is formed into a handle to assist in both the insertion and removal of the cassette from a warming unit.

6 Claims, 5 Drawing Sheets

INTRAVENOUS FLUID WARMING CASSETTE WITH STIFFENING MEMBER AND INTEGRAL HANDLE

BACKGROUND AND SUMMARY OF THE INVENTION

This invention is generally related to parenteral fluid warming systems and, more particularly, to the structure of a warming cassette that includes a stiffening frame with an attached fluid container and that is used in a parenteral fluid warming apparatus.

Fluid warming apparatuses, designed to warm and administer parentarel fluids and blood products (hereinafter "fluids"), are in common use. Generally, these fluids are administered using a disposable fluid container which includes a fluid pathway and one or more heat exchange surfaces. The fluid container may be made of plastic film material or thin metal. A warming cassette incorporates such a fluid container, imparting structural support to the container for handling and for being received and supported in a warming unit.

Specifics of a multi-layered fluid container compatible with a supporting cassette frame sturcture are discussed in a co-pending patent application Ser. No. 09/415,558, entitled "PRESSURE TOLERANT PARENTERAL FLUID AND BLOOD CONTAINER FOR A WARNING CASSETTE", invented by Augustine et al., Filed Oct. 8, 1999.

A warming cassette is placed into a warming unit to heat fluids as they flow through the fluid pathway. Heat is transferred to the fluid through the fluid container by contact with a heat source such as heated metal plates, heated liquid, or heated gas. Metal plate, "dry heat" exchanger warming units are widely known. However, in the last 10 to 15 years, water bath heat exchangers have become the norm in the United States.

While convenient to use, water bath heat exchangers can pose health risks. The warm water in these systems is often circulated for long periods of time without being changed or sterilized. The warm water provides an excellent growth medium for microbes. After several weeks of use, bacteria and fungi can be cultured from these water baths. For these reasons, a "dry heat" system is probably safest for warming medical fluids. However, there are significant fluid thermodynamic problems, as well as convenience, reliability, and cost issues that must be solved for a "dry heat" system to replace the water bath systems.

The American Association of Blood Banks (AABB) mandates that blood products and IV fluids must not be heated above a temperature of 42° C., so as to prevent blood cell damage and thermal injury to a patient. A temperature of 42° C. is easy to maintain under steady-state flow conditions, at low flow rates. However, as the flow rate of the fluid increases, the rate of heat transfer to the fluid must keep pace in order to achieve a target fluid temperature. The boost in the rate of heat transfer is most obviously achieved by using larger heaters and by increasing the temperature difference ($\Delta T$) between the heater and the fluid. Both solutions effectively drive more heat into the fluid. Unfortunately, these solutions are not necessarily effective when the fluid flow rates are highly dynamic. Large heaters and high temperature differentials are not responsive enough to sudden changes in fluid flow rates. For example, in the case of a sudden change from a high fluid flow rate to a low one, the high temperature limit can be exceeded, potentially causing thermal damage to the fluid or patient.

The problems of thermal efficiency and temperature responsiveness over a wide range of flow rates can be met by improving the thermal conductivity of the fluid cassette materials, and minimizing the thickness of the fluid at the point of heat transfer. This implies a thin, flat fluid container, constructed from properly selected materials.

Plastic film materials are commonly used in the manufacture of disposable fluid warming cassettes. However, plastic is a poor heat transfer material. Metal foils, or metal conduits have been used with plastic materials in warming cassettes to enhance thermal conductivity; however, it is difficult to bond metal to plastic materials, and leakage can occur along bonding seams between these materials. Further, metal foils generally increase the cost of cassette manufacturing.

Fluid temperature response may also be improved by reducing the thickness of the fluid channel in the fluid container. In this regard, the space between the heater plates is then reduced to be compatible with thin cassettes. Assume, for example, that an optimal balance between fluid flow resistance and heat transfer for a particular warming unit design yields a distance of 0.048 inches between the heater plates of the unit. It is very difficult to insert an appropriately dimensioned cassette into such a warming unit simply by sliding it between the warming plates. The plastic materials of which such cassettes are made impart little rigidity. Consequently, such a cassette may kink or tear when being slid into or out of such a small space. As a result, "clamshell" solutions have been proposed that spread the warming plates apart when a cassette is inserted or removed from a warming unit.

The limitations of the clamshell design are manifest. Moving parts add to the warming unit's cost, and reduce reliability. It is very difficult to maintain an accurate 0.048 in. spacing across the entire plate surface, when hinges, clasps, and other moving parts are required. Finally, insertion of the cassette into such a warming system becomes a multi-step process, which is both time consuming and inconvenient.

Other problems occur with the use of plastic fluid containers in fixed plate warming units. For example, the fluid channel formed between the ,plastic films of a fluid container must be contained entirely within the space between the heater plates. However, some portion of the cassette must extend outside of the heater plates in order to provide structure that can be grasped to extract the cassette. If the portion of the cassette that extends outside of that space includes an unsupported portion of the fluid container, the container can rupture when the fluid pressure is increased to increase the flow rate.

It would be advantageous if an efficient and low cost fluid cassette could be developed for a "dry heat" parenteral fluid warming system. Advantage would be gained if the fluid cassette permitted the rapid heating of parenteral fluid under high pressures. Further, it would also be advantageous if the cassette could be made rigid, yet thermally conductive, without the use of metal.

It would be advantageous if a cassette fluid container could be made with plastic walls stiff enough for insertion in between close-set parallel warming plates of a warming unit, yet thin enough to efficiently transfer heat from the plates to the fluid.

It would be advantageous if the above-mentioned cassette could be easily inserted into and removed from the warming unit without being kinked or torn. It would further be advantageous if the cassette had a handle for insertion of the cassette between the warming plates of a fluid warming unit. It would be advantageous if the above-mentioned cassette handle extended outside the unit for convenient handling.

SUMMARY OF THE INVENTION

Accordingly, a warming cassette for parenteral fluids, used in a parenteral fluid warming system, is provided. The cassette comprises a flexible fluid container made from thermally conductive material and attached to a planar frame structure, which imparts structural rigidity to stiffen and support the fluid container. The fluid container and the frame structure are all of a piece, permanently bonded, joined or. connected together in a unitary, integrated structure. The frame structure is in the shape of a planar figure bounded by sides. Preferably the figure is a quadrilateral, with sides; a distal end, and a proximal end. A handle is provided on the proximal end. A fluid container is disposed inside the shape of the frame structure, attached along its periphery to the sides and ends. Optionally, the container could be attached to just the sides or just the ends. The handle provides an element that may be grasped to manipulate the cassette for insertion into and extraction from a warming unit.

Optionally, the warming cassette is provided with a keying mechanism that prevents it from being inserted either upside down, or backwards in a warming unit. The keying mechanism also prevents the cassette from being inserted too far into the warming unit. The keying mechanism comprises lands on the sides of the frame structure. To key the cassette, the lands mate with corresponding grooves in the warming unit.

DETAILED DEPICTION OF THE PREFERRED EMBODIMENT

This invention is a cassette for warming fluids during intravenous infusion. The cassette is designed for use with a "dry heat" warming unit in which heater plates are disposed in a parallel, spread-apart orientation, separated by a thin laminar space. The cassette is received in the space between the heater plates, in close contact with the heater plates.

The warming cassette has a unitary integral structure that includes two portions: a frame structure, and a fluid container attached, or joined, to the frame structure. The fluid container portion of the cassette is made of two sheets of thermally conductive plastic film material. Preferably, the two sheets of plastic film material are bonded together in a pattern which creates a fluid channel between the sheets. A fluid channel with a serpentine pattern is illustrated, although other patterns are contemplated. Preferably the plastic film is 0.004 in. (4 mil) thick, or less.

Figure 1A:
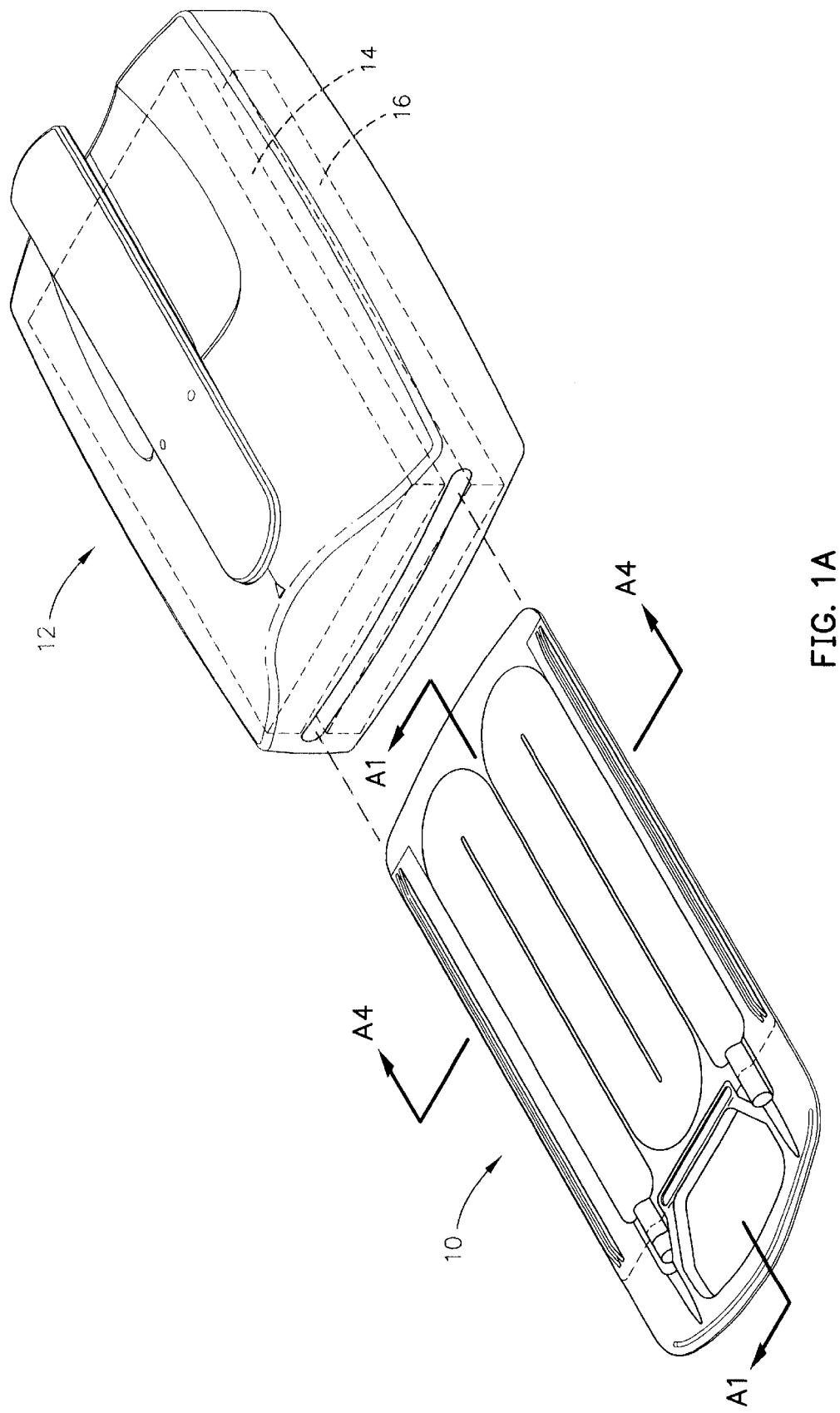
FIG. 1A is a perspective view of a warming cassette according to this invention for use in an intravenous fluid warming system.

FIG. 1A is a perspective illustration of a warming cassette 10 according to the invention for use with an intravenous fluid warming unit 12. The warming unit 12 is a "dry heat" unit. with warming plates 14 and 16. The plates 14 and 16 are maintained spread apart at a fixed distance, and the cassette 10 is inserted between the plates 14 and 16 so that the fluid in the cassette 10 is heated before infusion into a body.

Figure 2A:
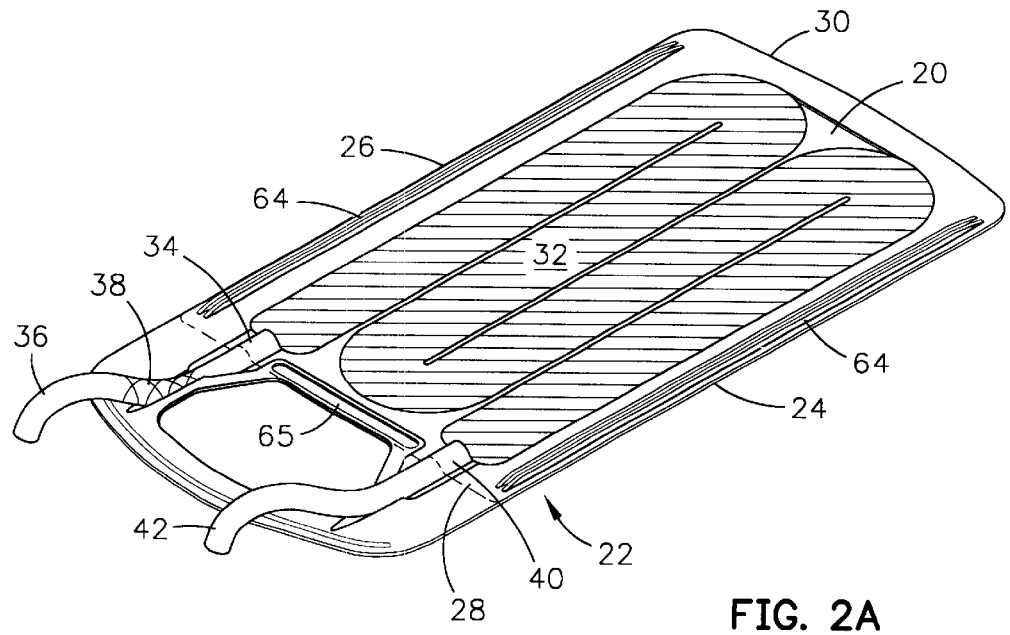
FIG. 2A is a more detailed depiction of the warming cassette of FIG. 1A.
Figure 2B:
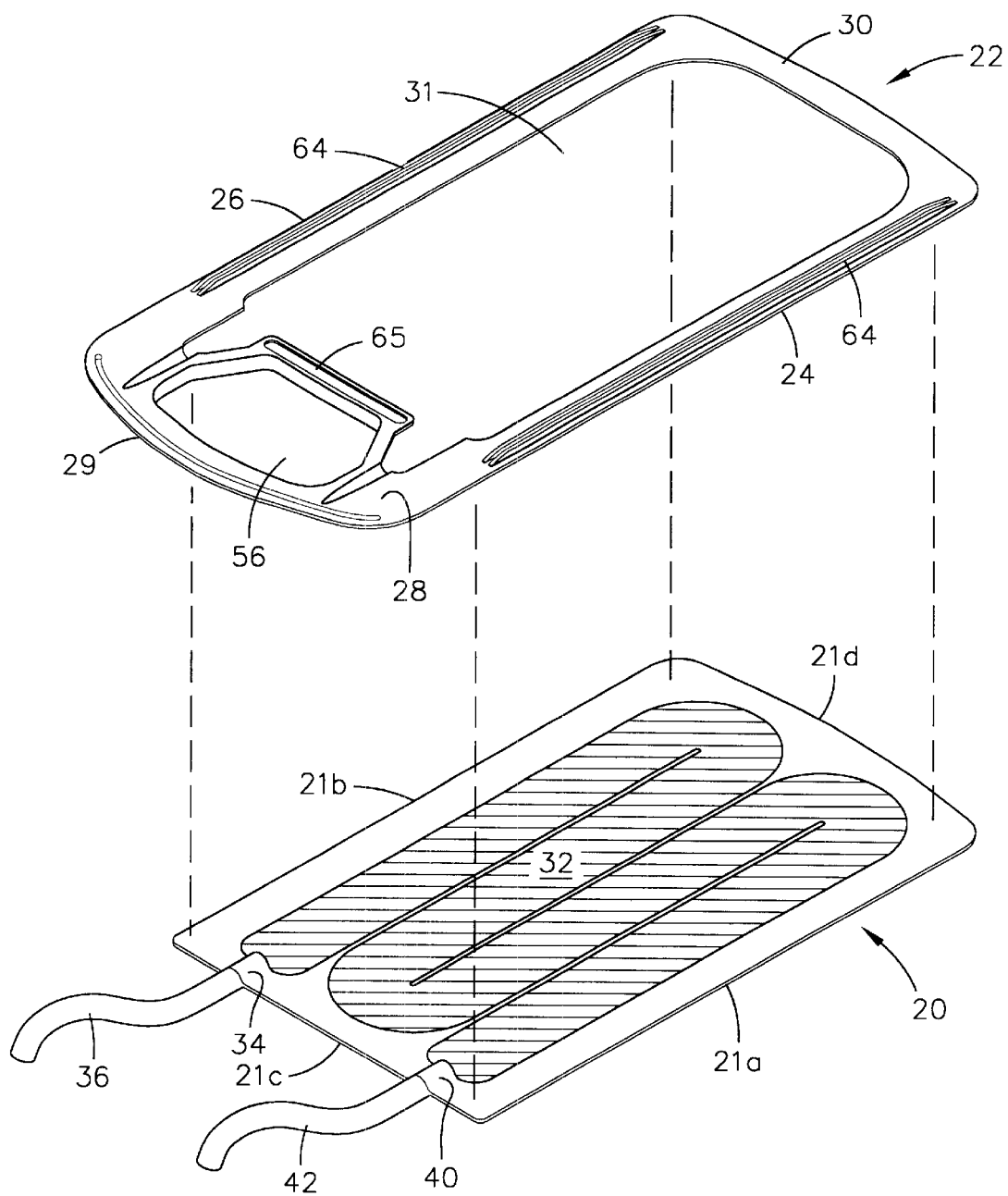
FIG. 2B is an exploded view of the warming cassette of FIG. 1A.

FIG. 2A is a more detailed depiction of the warming cassette 10 of FIG. 1A; FIG. 2B is an exploded view of the cassette 10 showing two of its elements. The cassette 10 comprises a flexible fluid container 20 and a frame structure 22 to which the fluid container 20 is attached, joined, or bonded. The frame structure 22 stiffens the cassette within a first plane represented by orthogonal X and Y axes. The X and Y axes are referred to herein as first and second directions, respectively. Likewise, the fluid container 20 is substantially planar and disposed in the first plane. The frame structure 22 is considered to be rigid with respect to the flexible fluid container 20. However, the frame structure 22 also has some degree of flexibility. Preferably, the frame structure 22 is semi-rigid.

The frame'structure 22 is in the shape of a planar figure bounded by sides; preferably the figure is a closed figure. For example, FIGS. 2A and 2B, the figure is a quadrilateral having sides 24 and 26, a distal end 30, and a proximal end 28. The figure of the quadrilateral defines an opening 31 within which the fluid container 20 is received. The fluid container 20 has a periphery including opposing, parallel sides 21a and 21b, and opposing, parallel ends 21c and 21d. The cassette 10 is assembled by receiving the fluid container 20 within the opening 31 and joining the fluid container 20 to the frame structure 22 by bonding, or otherwise permanently joining or connecting, the periphery 21a, 21b, 21c, and 21d of the fluid container 20 to the sides and ends 24, 26, 28, and 30 of the frame structure 22. Alternatively, the peripheral bonds could include just the sides 24 and 26, or just the ends 28 and 30. As a consequence of such bonding, joining, or connecting, the fluid container cannot be separated from the frame structure. The result, best seen in FIG. 2A is a unitary integrated warming cassette structure that may be handled, manipulated, or otherwise used or processed as a single piece. The inventors contemplate that the quadrilateral shape of the frame structure 22 may be practiced in an alternate embodiment in which distal end 30 is omitted, or is not continuous with the sides 24 and 26. As best seen in FIG. 2A, the sides 24 and 26 are oriented, and provide stiffness in the first direction (X-axis) while the ends 28 and 30 are oriented, and provide stiffening in the second direction (Y-axis). Taken together, the sides 24 and 26 and the ends 28 and (optionally,end 30) provide stiffness generally in the X Y plane.

Figure 1B:
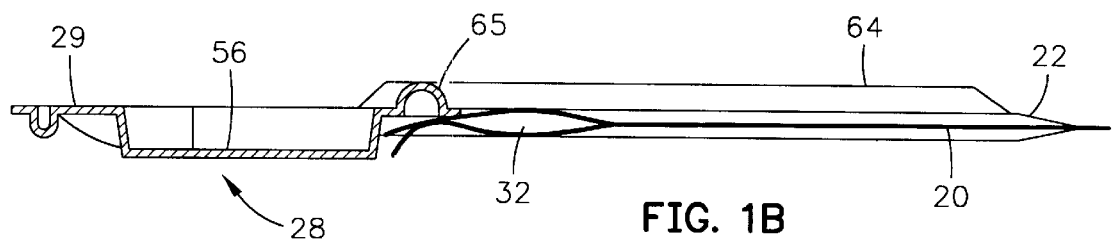
FIG. 1B is side sectional view of the cassette taken along A1—A1 of FIG. 1B.

In some aspects of the invention the proximal end 28 includes a handle portion 29, formed to be manipulable by hand. That is, the proximal end 28 is given sufficient surface area, extending away from the fluid container 20 to accommodate finger purchase. When the cassette 10 is engaged with warming device 12 (see FIG. 1), the handle portion 29 is not received (at least, not entirely received) between the plates 14 and 16. The handle portion 29 remains accessible while the rest of the cassette is being heated between plates 14 and 16.

Figure 3A:
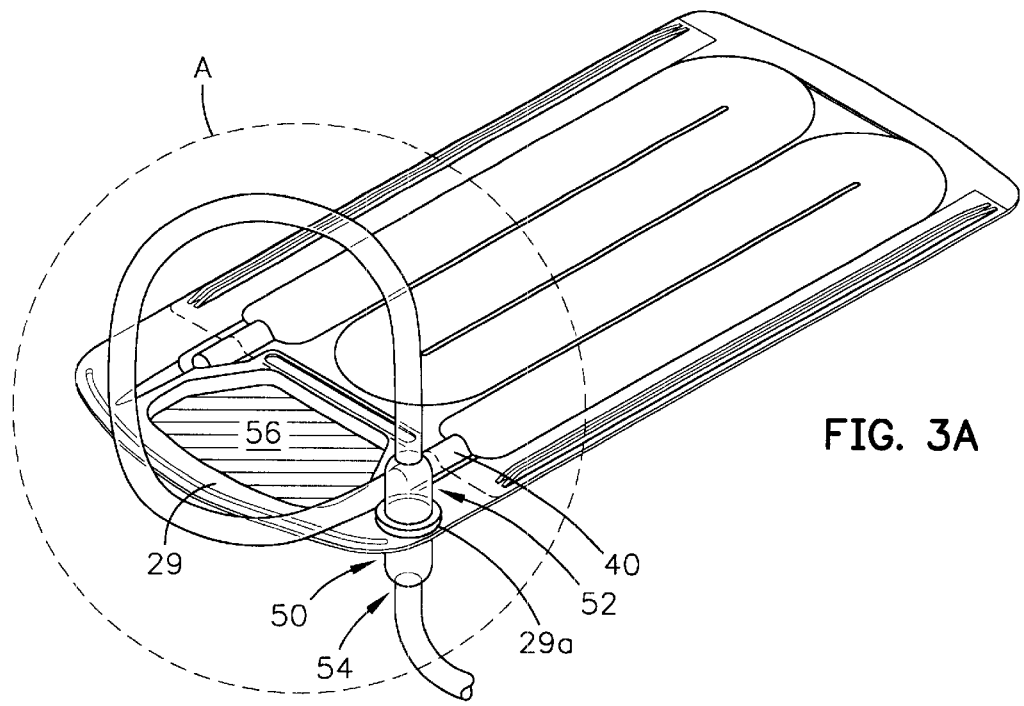
FIGS. 3A and 3B illustrate the warming cassette 10 of FIG. 1A, detailing an optional bubble trap feature.

The handle portion 29 serves several purposes:
  first, the handle portion 29 maintains the sides 24 and 26 in proper alignment and position for easy, one handed indexing with the warming unit;
  second, the handle portion 29 may include a hole 29a for accommodating and holding a bubble trap which is part of the tubing connected to the fluid outlet (see FIG. 3A);

third, the handle portion 29 includes a stopping mechanism 65 which mechanically prevents handle portion 29 from entering fluid warming unit 12 and assures proper insertion depth (see FIGS. 1B, 2A, 2B, 3A and 3B);

fourth, the handle portion 29 preferably includes a mechanism 38 for supporting fluid inlet and fluid outlet tubing (see FIG. 2A), and providing strain relief preventing undue tension being applied to the tubing. Without this kind of strain relief, there is the risk of tension on the tubing, resulting in tearing the plastic film material. Attaching the tubes helps to prevent kinking of the tubing as it leaves the warming unit; and fifth, the handle portion 29 includes a substantially flat area 56 which may be used for labeling (see FIG. 3A). Since the majority of the cassette 10 is inside the warming unit during use, it is convenient to have labeling visible to the user even during use. Handle portion 29 is always external to the warming unit and, therefore, is an ideal platform for such labeling.

The frame structure 22 can be formed from a material selected from the group consisting of polyester, polyamide (Nylon®, DuPont), polyethylene glycol terephthalate (Mylar®, DuPont), and ionomer resins (Surlyn®, DuPont). The frame structure 22 can be manufactured by die cutting, injection molding, and thermal processes.

The fluid container 20 can be made from one or more materials selected from the group consisting of polyvinyl chloride (PVC), polyurethane, polypropylene, polyethylene, polyester, and other polymeric materials.

The fluid container 20 includes a fluid channel 32 and at least a first port 34 for fluid communication with the fluid channel 32, which is highlighted with cross-hatched lines in FIGS. 2A and 2B. A first tube 36 is joined to the first port 34. Optionally, the first tube is attached to the frame structure 22 at its proximal end 28. Alternately, the first tube 36 is, at least partially, formed to be an integral part of the handle portion 29. In FIG. 2A, the area of attachment is represented with double cross-hatched lines and labeled with reference numeral 38. The fluid container 20 also includes a second port 40 in fluid communication with the fluid channel 32. A second tube 42 is joined to the second port 40.

Figure 3B:
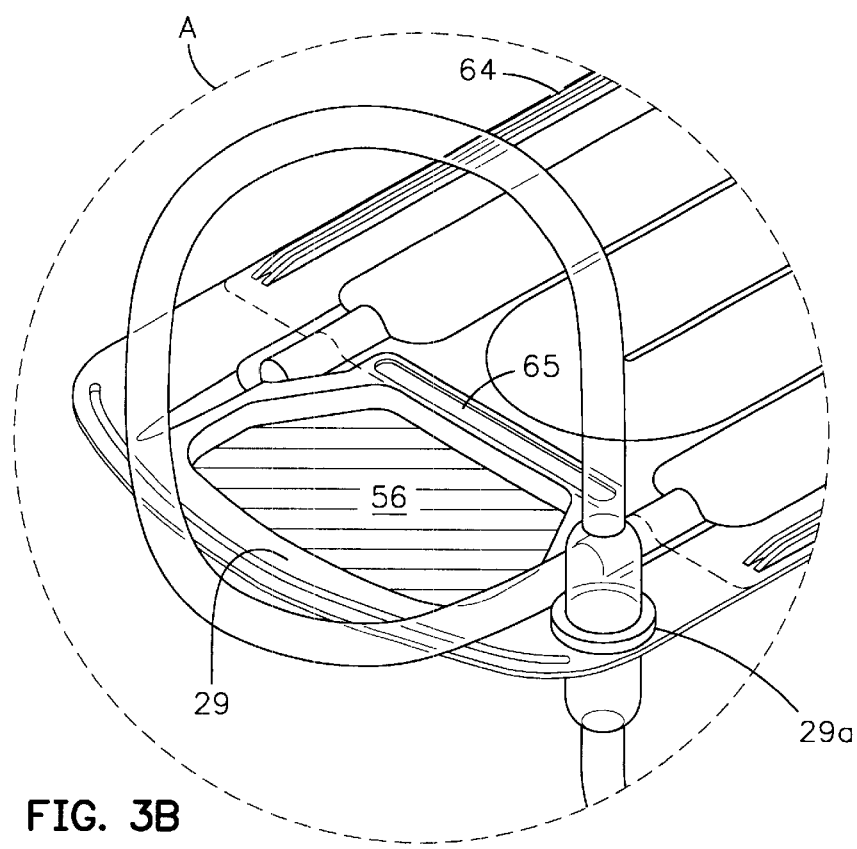

FIGS. 3A and 3B illustrate the warming cassette 10 of FIG. 1, detailing an optional bubble trap feature. FIG. 3B is an enlargement of Section A of FIG. 3A. The warming cassette 10 optionally includes a bubble trap 50 attached to the handle portion 29 for support. The bubble trap 50 traps any air bubbles that may have inadvertently been introduced into the inlet tubing from the IV bag or may have been created by "out-gassing" during the warming of the fluids. The bubble trap 50 has an input 52 connected to the second port 40. The bubble trap 50 has an output 54 to supply fluid, and a gas exhaust port (not shown) to vent gases escaping from the communicated fluid. The output 54 is operatively connected to the patient's IV catheter (not shown).

The bubble trap 50 can be mechanically attached or bonded through thermal, adhesive, or chemical means to the handle portion 29. Attaching the bubble trap 50 to the handle portion 29 makes it less likely that the trap 50, or its associated tubing will be inadvertently disconnected from the cassette 10.

The handle portion 29 optionally includes a label surface 56, highlighted with cross-hatched lines in FIGS. 3A and 3B. The cassette 10 then may receive a label (not shown) overlying the second stiffening member label surface 56. The label can be visible to the eye, or configured for electronic identification, such as a bar code.

Figure 4A:
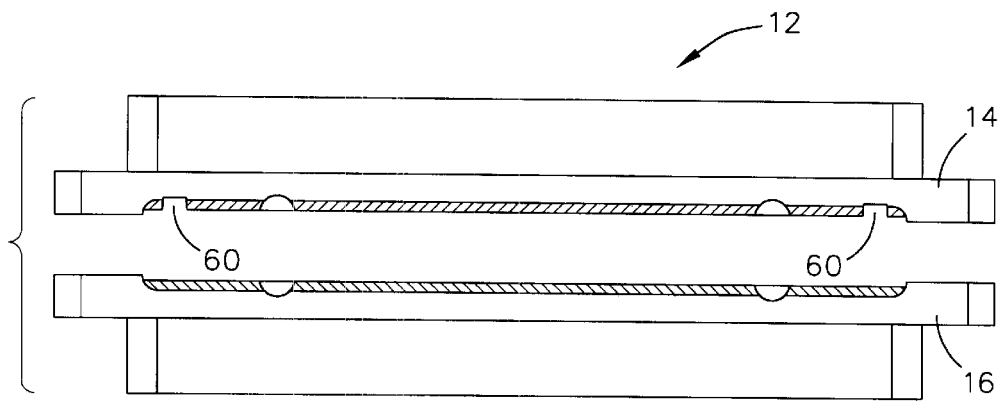
FIGS. 4A through 4C illustrate details of the present invention keying system used to selectively orient the cassette in the warming apparatus.
Figure 4B:
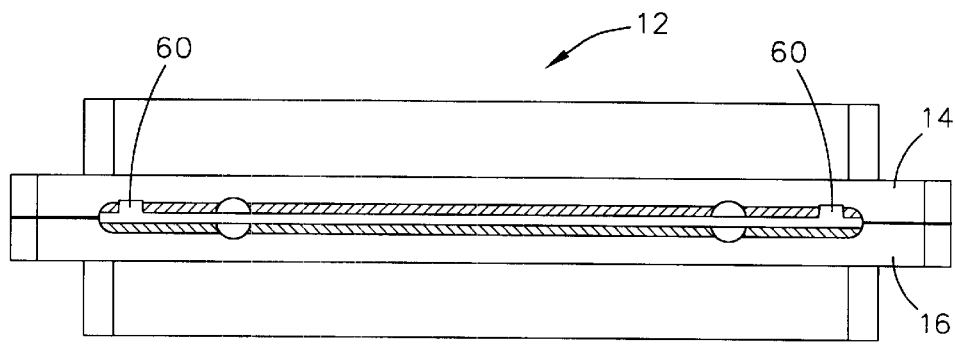
Figure 4C:
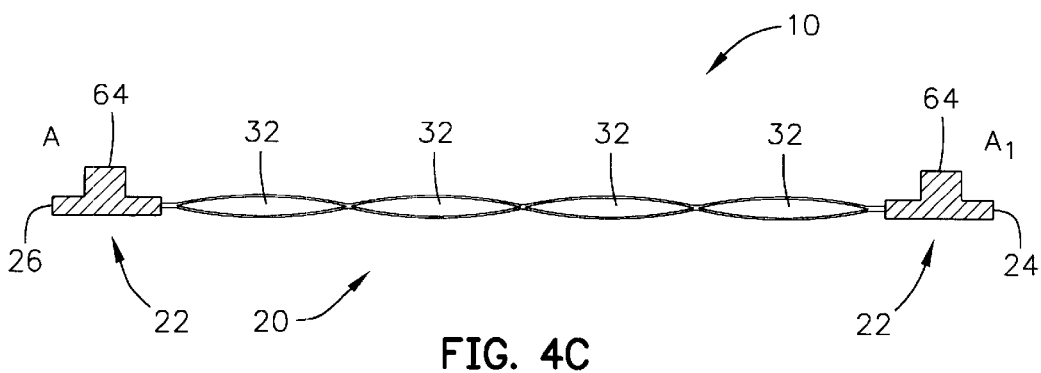

FIGS. 4A through 4C illustrate details of keying elements used to orient the cassette 10 in the warming unit 12. The intravenous warming unit 12 includes the first and second opposing warming plates 14 and 16, adapted to accept the warming cassette 10 in a first orientation. FIG. 4A is a simplified end view of the warming unit 12. The warming plates 14 and 16 have been separated for the purpose of clarifying the invention. Two grooves 60 are formed in the upper plate 14 to cooperate with a key mechanism on the warming cassette 10. FIG. 4B illustrates the warming unit 12 with the warming plates 14 and 16 assembled for normal operation.

Refer now to FIGS. 1A–3B and 4C. FIG. 4C is a sectional view taken along A4—A4 of FIG. 1A. In these figure, there are illustrated two lands 64 that act as a key mechanism with the grooves 60 to mate the cassette 10 with the warming plates in a predetermined orientation. Preferably, the lands 64 are formed integrally with the sides 24 and 26, and extend longitudinally thereon. When the warming cassette 10 is received between the plates 14 and 16, the lands 64 key the warming cassette 10 by permitting the cassette to be inserted or slid into the space between the plates only if the lands 64 are received in the grooves 60. Otherwise, the lands 64 will prevent the cassette from being inserted into the warming unit 12 between the plates 14 and 16.

Referring to FIGS. 1B–3B, a stop mechanism is illustrated in the form of a ridge 65 that extends parallel to the distal end 28 on an upper surface of the handle portion 29. The ridge 65 is high enough to contact the upper plate 14 when the fluid pathway 32 is fully received between the plates 14 and 16; this contact stops the cassette from being inserted any further between the plates 14 and 16. Manifestly another, or an alternate ridge can be provided on the lower surface of the handle portion 29.

The unitary, integrated warming cassette 10 of FIGS. 1A and 2A can be inserted into the warming unit 12 by a user, employing one hand to grasp the integral handle portion 29, orienting the warming cassette 10 so that the lands 64 are aligned with the grooves 60, inserting the distal end 30 between the plates 14 and 16 and sliding the warming cassette 10 inwardly between the plates 14 and 16 until the stopping mechanism 65 halts further insertion.

Other variations and embodiments of the prevent invention will occur to those skilled in the art with reflection upon the disclosed examples of the present invention cassette fluid container and formation of such a cassette fluid container.

What is claimed is:

1. A method of operating a parenteral fluid warming system that includes a warming unit having parallel heating plates with alignment grooves and a fluid warming cassette with a quadrilateral frame structure having a distal end, a proximal handle, alignment lands, and a stop mechanism near the proximal handle, the warming cassette further including a fluid container with a fluid pathway, in which the fluid container is joined to the frame structure, the method including:

grasping the proximal handle;

orienting the lands with the grooves;

inserting the distal end between the heating plates; and sliding the warming cassette between the heating plate until the stop mechanism engages the warming unit.

2. The method of claim 1, further including transferring heat from the heating plates to the fluid container.

3. The method of claim 1, further including providing parentarel fluid to the fluid pathway.

4. The method of claim 3, wherein providing includes providing the parentarel fluid under pressure.

5. The method of claim 3, further including transferring heat from the heating plates to the fluid container.

6. The method of claim 5, wherein providing includes providing the parentarel fluid under pressure.

* * * * *